(12) United States Patent
Schmid et al.

(10) Patent No.: US 8,562,133 B2
(45) Date of Patent: Oct. 22, 2013

(54) SIMULATOR FOR USE IN OPHTHALMOLOGICAL MEASUREMENTS

(75) Inventors: Stefan Schmid, Heilsbronn (DE); Berndt Warm, Schwaig (DE)

(73) Assignee: WaveLight GmbH, Erlangen (DE)

( * ) Notice: Subject to any disclaimer, the term of this patent is extended or adjusted under 35 U.S.C. 154(b) by 257 days.

(21) Appl. No.: 12/894,314

(22) Filed: Sep. 30, 2010

(65) Prior Publication Data

US 2012/0081663 A1    Apr. 5, 2012

(51) Int. Cl.
*A61B 3/00* (2006.01)
*A61B 3/10* (2006.01)

(52) U.S. Cl.
USPC ............ 351/204; 351/200; 351/209; 351/214

(58) Field of Classification Search
USPC .......................... 351/204–205, 208–209, 214
See application file for complete search history.

(56) References Cited

U.S. PATENT DOCUMENTS

| | | | |
|---|---|---|---|
| 5,661,538 A * | 8/1997 | Carter | 351/237 |
| 5,900,923 A * | 5/1999 | Prendergast et al. | 351/221 |
| 6,257,721 B1 * | 7/2001 | Hayashi et al. | 351/204 |
| 6,576,013 B1 | 6/2003 | Budman et al. | |
| 2002/0036749 A1 * | 3/2002 | Isogai | 351/206 |
| 2005/0254008 A1 * | 11/2005 | Ferguson et al. | 351/205 |
| 2006/0250684 A1 * | 11/2006 | Sander | 359/368 |
| 2008/0094689 A1 * | 4/2008 | Van Gorkom et al. | 359/296 |
| 2008/0201329 A1 * | 8/2008 | Xie | 707/6 |
| 2008/0309870 A1 | 12/2008 | Chernyak | |
| 2010/0220897 A1 * | 9/2010 | Ueno et al. | 382/115 |
| 2010/0231857 A1 * | 9/2010 | Chernyak | 351/206 |

FOREIGN PATENT DOCUMENTS

WO    2009/129829 A1    10/2009

* cited by examiner

*Primary Examiner* — Jordan Schwartz
(74) *Attorney, Agent, or Firm* — Keiko Ichiye

(57) ABSTRACT

A simulator to be used in ophthalmological measurements includes a display apparatus and a control device. The control device is adapted to control the display apparatus in such a manner that the display apparatus displays an image that is adapted to simulate the arrangement of a pupillary midpoint relative to a reference structure.

13 Claims, 2 Drawing Sheets

SIMULATOR FOR USE IN OPHTHALMOLOGICAL MEASUREMENTS

The invention relates to a simulator for use in ophthalmological measurements.

BACKGROUND OF THE INVENTION

In ophthalmological research and practice an extremely wide range of measuring devices are employed in order to measure properties of eyes. With many of these measuring instruments, electromagnetic radiation—in particular, light—is beamed onto and/or into an eye to be examined, and the influence exerted on the electromagnetic radiation by the elements of the eye and/or the influence exerted on the eye by the electromagnetic radiation is/are ascertained, in order to be able to draw inferences as to properties of the eye and, in particular, pathological changes. For example, for the purpose of preparing a refractive surgical treatment of an eye it is necessary to examine the reaction to light stimuli of the eye to be treated. In particular, a displacement of the pupillary centre as a function of the pupillary diameter, the so-called pupil-centre shift, has to be ascertained, since the pupillary midpoint customarily serves in refractive surgery as reference point for eye-tracker systems and for the positioning of an ablation profile. For such measurements of pupil-centre shift, a pupillometer described in US 2008/0309870 A1, for example, may come into operation.

Measurement data generated by ophthalmological measuring instruments must in many cases be checked and verified by appropriate reference measurements. Furthermore, reference measurements are required for calibrating the measuring instruments or in connection with the development of new instruments and measuring techniques. For measuring instruments, the functional principle of which is based on the examination of the influence exerted on electromagnetic radiation beamed onto and/or into an eye to be examined by means of substantially static elements of the eye such as, for example, the cornea or the lens, for this purpose models of the eye that are described, for example, in DE 10 2006 030 574 A1 or in WO 2009/129829 A1 may be employed, which, inter alia, include simulations of the cornea and of the lens of a human eye. The simulations consist of a synthetic material that has been doped with scattering substances in order to imitate the scattering properties of the real prototypes. However, by reason of their static structure these known eye models are not suitable to be used for reference measurements with a pupillometer that serves to examine the reaction of an eye to light stimuli, i.e. the influence exerted by light stimuli on the pupillary diameter and on the position of the pupillary centre.

BRIEF SUMMARY OF THE INVENTION

An object underlying the invention is to make available a simulator that is suitable for use in reference measurements with a pupillometer.

This object is achieved by a simulator for use in ophthalmological measurements, the simulator including a display apparatus and a control device. The control device, which, for example, may be designed in the form of an electronic control device, is adapted to control the display apparatus in such a manner that the display apparatus displays an image that is suitable to simulate the arrangement of a pupillary midpoint relative to a reference structure. In particular, the electronic control device is adapted to control the display apparatus of the simulator according to the invention in such a manner that the display apparatus displays in succession various images that are suitable to simulate various arrangements of a pupillary midpoint relative to a reference structure. In other words, the simulator according to the invention does not have a static structure but enables, through the use of a display apparatus for representing on the display apparatus various images simulating the arrangement of a pupillary midpoint relative to a reference structure, a simple and convenient simulation of a pupil-centre shift.

The images displayed by the display apparatus of the simulator can be gauged by a pupillometer. Subsequently the measured values registered by the pupillometer can be compared with the position of the pupillary midpoint, known from the structural design of the simulator and also from the programming of the control device, in the image represented by the display apparatus of the simulator, and the findings obtained in the course of this comparison can, for example, be utilised for verifying the measured values ascertained by the pupillometer and/or for calibrating the pupillometer. The simulator according to the invention can consequently be drawn upon for reference measurements with a pupillometer or with a higher-order diagnostic or therapeutic instrument having a pupillometric function. In particular, the simulator according to the invention can be used for testing the reaction of an eye-tracking system to a moving pupil and hence for testing the functionality of the eye-tracking system.

The control device is preferentially adapted to control the display apparatus in such a manner that the display apparatus displays in succession a plurality of images that are adapted to simulate a variation of the arrangement of a pupillary midpoint relative to a reference structure that has been adapted to the physiological response of a natural eye. In other words, the control device is preferentially programmed in such a way that it is adapted to control the display apparatus in such a manner that the images displayed on the display apparatus simulate the pupil-centre shift of a natural eye reproducibly. A simulator that enables a simulation, as realistic as possible, of the pupil-centre shift of a natural eye permits the implementation of realistic reference measurements. The results of reference measurements carried out under realistic conditions can be transferred particularly well to the real use of the ophthalmological diagnostic or therapeutic instrument.

The control device is preferentially adapted to control the display apparatus in such a manner that the display apparatus displays an image that includes a representation of an iris. An iris is comparatively easy to represent on the display apparatus, in which connection an inner margin of the iris may be regarded as a boundary margin of a pupil. By variation of the shape of the iris in the image represented by the display apparatus, a variation of the pupillary diameter and/or a variation of the arrangement of a pupillary midpoint relative to a reference structure can consequently be simulated in straightforward manner.

Under the control of the control device of the simulator according to the invention, various reference structures may be utilised for the variable relative positioning of the pupillary midpoint. For example, the control device of the simulator according to the invention may be adapted to control the display apparatus in such a manner that the display apparatus displays an image that is adapted to simulate the arrangement of a pupillary midpoint relative to an apex of a cornea. Such a configuration of the simulator is particularly advantageous when the ophthalmological diagnostic or therapeutic instrument with which reference measurements in respect of the simulator are to be performed customarily draws upon the apex of the cornea by way of reference point in the course of a measurement of the pupil-centre shift.

Additionally or alternatively, however, the control device may also be adapted to control the display apparatus in such a manner that the display apparatus displays an image that is adapted to simulate the arrangement of a pupillary midpoint relative to an eye structure differing from an apex of a cornea. For example, at least one of an outer iris margin, iris structures and blood-vessel structures may be drawn upon, in addition to or as an alternative to an apex of a cornea, by way of reference structures for the positioning of the pupillary midpoint. For this purpose the control device may have been programmed in such a way that it is adapted to control the display apparatus in such a manner that the display apparatus displays an image that includes eye structures such as, for example, at least one of an iris with an outer iris margin, iris structures and blood-vessel structures. From the structural design of the simulator and also from the programming of the control device, the variable position of the pupillary midpoint in the image represented by the display apparatus of the simulator relative to the chosen reference structure(s) is then known and may be compared with the measured values that are obtained by a diagnostic or therapeutic instrument gauging the images displayed by the display apparatus of the simulator.

By virtue of the possibility of selecting various and/or several reference structures, the simulator may be adapted particularly flexibly to variously configured diagnostic or therapeutic instruments. This means that diagnostic or therapeutic instruments that in real operation utilise at least one of an outer iris margin, iris structures and blood-vessel structures by way of reference structure may also gauge the simulator by utilising at least one of an outer iris margin, iris structures and blood-vessel structures by way of reference structure(s).

In a preferred embodiment of the simulator according to the invention, the display apparatus includes a self-luminous display. For example, an OLED (organic light-emitting diode) display may come into operation by way of self-luminous display. In the case where a self-luminous display is employed in the display apparatus of the simulator according to the invention, an influence exerted on the image represented on the display apparatus by external illumination or by electromagnetic radiation directed onto the simulator by an ophthalmological diagnostic or therapeutic instrument is minimised. This enables an increase in the accuracy of measurement.

Furthermore, the display apparatus of the simulator according to the invention may include a foil display. By means of a foil display, the real shape of an eye can be simulated, as a result of which the design of the simulator becomes still more realistic.

The simulator according to the invention may further include at least one of a lens simulation, an eye-chamber simulation and a cornea simulation. These simulations may consist of a synthetic material and, if desired, may contain diffusers, by means of which the scattering properties of the simulations may be adapted to the scattering properties of their natural prototypes. Furthermore, the simulations may exhibit fluorescent properties. The positions of the simulations in the simulator are preferentially adapted to the positions of their natural prototypes in a natural eye. The display apparatus is therefore positioned in a simulator including a lens simulation, an anterior-eye-chamber simulation and a cornea simulation, preferentially between the anterior-eye-chamber simulation and the lens simulation. The cornea simulation, on the other hand, is arranged on a side of the anterior-eye-chamber simulation facing away from the display apparatus.

Optical elements serving, in particular, for simulating an anterior portion of an eye, i.e. an anterior eye chamber and a cornea for example, are preferentially designed in such a way that the implementation of at least one of topographical measurements with a Placido system and Scheimpflug measurements in respect of the simulator is/are possible. For this purpose these optical elements preferentially consist of materials that have been chosen in such a way that mirror effects and/or differences in refractive index at the relevant illumination wavelengths and measurement wavelengths do not result in perturbations of the measurements. Furthermore, the surfaces of these optical elements may be provided with appropriate surface coatings and/or may be made antireflective, in order to avoid perturbations of the measurements. It will be understood that the configuration of the simulations, just like the programming of the control device and the image representation on the display apparatus, may be adapted to the specific configuration of an ophthalmological diagnostic or therapeutic instrument with which the simulator is to be gauged.

In a preferred embodiment of the simulator according to the invention, the display apparatus exhibits an aperture by which, in operation of the simulator, at least a portion of a pupil is simulated. In the region of the aperture formed in the display apparatus a lens simulation may be arranged. A simulator configured in such a manner is distinguished by particular closeness to reality.

Finally, the simulator according to the invention may include a brightness sensor which is adapted to measure the intensity of ambient light and to communicate signals that are characteristic of the intensity of ambient light to the control device. The control device may then be adapted to control the display apparatus in such a manner that the display apparatus displays an image that is suitable to simulate the arrangement of a pupillary midpoint relative to a reference structure as a function of a signal that is registered by the brightness sensor and that is characteristic of the intensity of ambient light. In other words, the control device may be adapted to control the display apparatus in such a manner that the display apparatus displays an image that is suitable to simulate an arrangement of a pupillary midpoint relative to a reference structure in a manner adapted to the physiological response of a natural eye, as a function of the intensity of ambient light. A simulator equipped with a brightness sensor and with an appropriately programmed control device is adapted to simulate particularly realistically the variation in pupillary diameter and the pupil-centre shift of a natural eye as a function of the intensity of ambient light.

BRIEF DESCRIPTION OF THE DRAWINGS

A preferred embodiment of the invention will now be elucidated in more detail on the basis of the appended schematic drawings, in which.

DETAILED DESCRIPTION OF PREFERRED EMBODIMENTS

Figure 1:
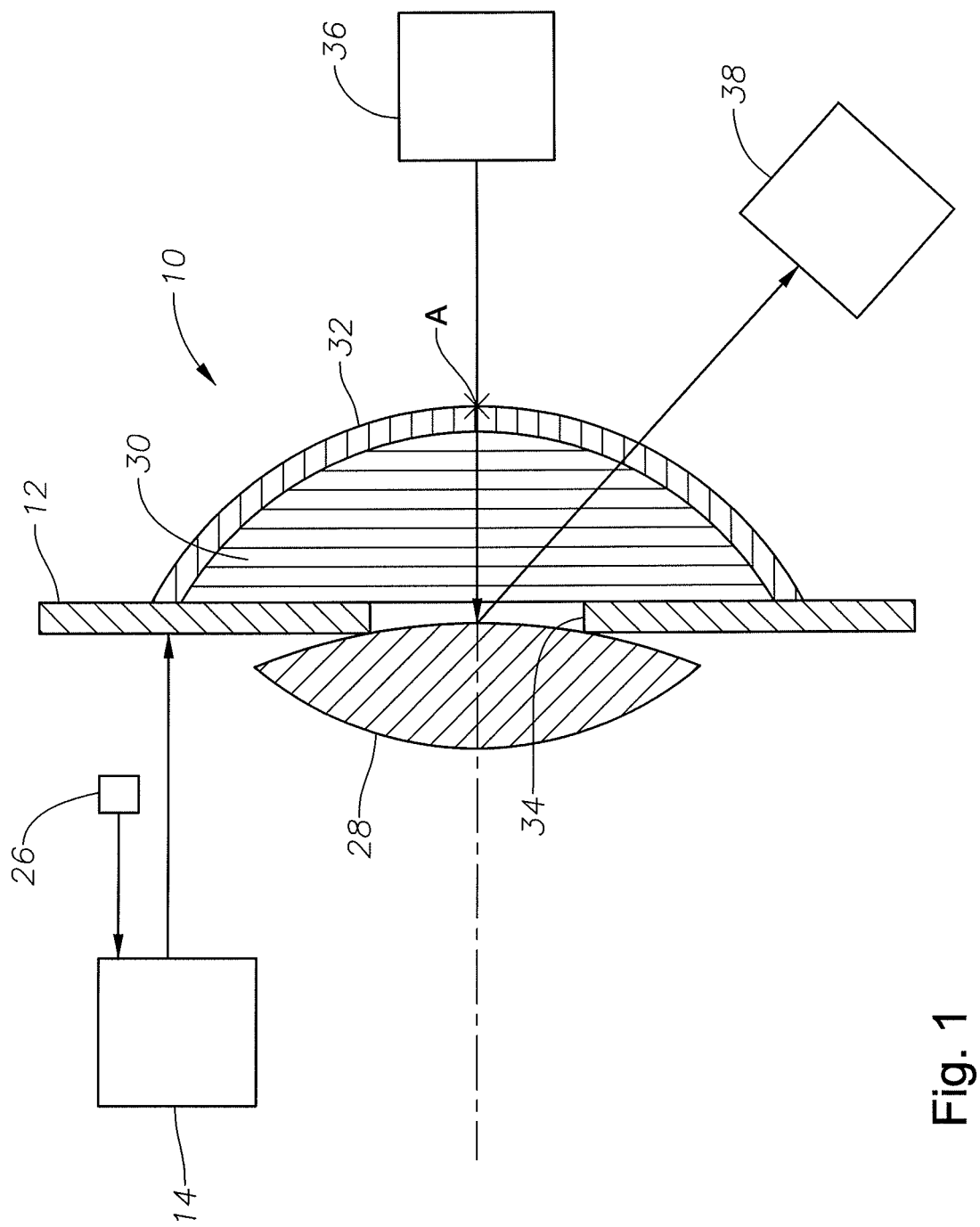
FIG. 1 shows a cross-sectional representation of a simulator in use in an ophthalmological measurement and FIGS. 2a and b show two front views of the simulator according to FIG. 1.

A simulator denoted generally by 10 in the Figures that, as represented in FIG. 1, is suitable for use in ophthalmological measurements includes a display apparatus 12 which is designed in the form of a self-luminous, programmable OLED display. The display apparatus 12 is controlled by means of an electronic control devoice 14 illustrated schematically in the Figures. As can best be discerned in FIGS. 2a and b, the control device 14 controls the display apparatus 12 in such a manner that the display apparatus 12 displays an image that includes the representation of an iris 16 as well as representations of iris structures 18 and also blood-vessel structures 20.

An inner margin 22 of the iris 16 represented on the display apparatus 12 defines an outer margin of a representation of a pupil 24. The display apparatus 12 accordingly displays an image that is suitable to simulate the arrangement of a pupillary midpoint P relative to a reference structure, in which connection an apex of a cornea and/or other eye structures—such as, for example, an outer iris margin 23 and/or the iris structures 18 and/or blood-vessel structures 20 shown in FIGS. 2a and 2b—may be drawn upon by way of reference structure. What is essential is merely that the reference structure remains static in the event of a variation in the pupillary diameter and in relation to, where appropriate, an associated variation in the position of the pupillary midpoint P.

Figure 2A:
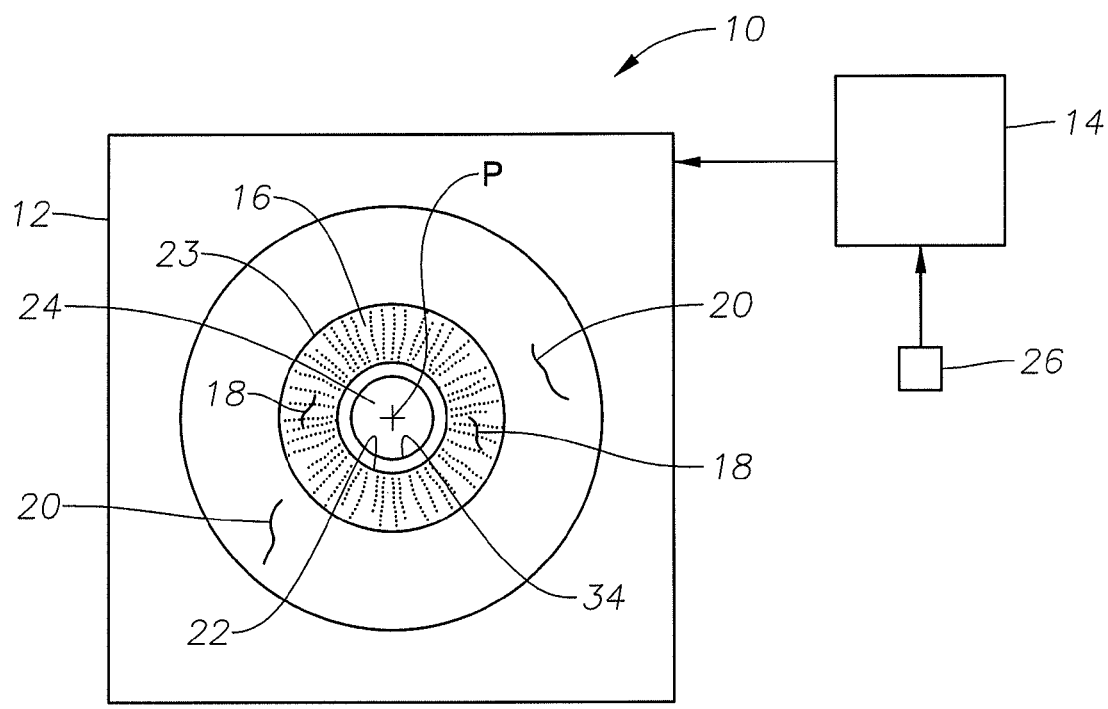

In particular, the control device 14 controls the display apparatus 12 in such a manner that the display apparatus 12, as illustrated in FIGS. 2a and b, displays in succession various images that are suitable to simulate a variation of the pupillary diameter and an associated variation in the arrangement of the pupillary midpoint P, i.e. a pupil-centre shift relative to the chosen reference structure. This is brought about by the shape of the iris 16 represented on the display apparatus 12, and hence the shape of the pupillary representation 24 bounded by the iris representation 16 relative to the chosen reference structure, being varied.

In order to enable a simulation of a pupil-centre shift adapted to the physiological response of a natural eye, the simulator 10 includes a brightness sensor 26. The brightness centre 26 has been set up to register the intensity of ambient light and to communicate a signal that is characteristic of the intensity of ambient light to the electronic control device 14. Furthermore, the control device 14 is programmed in such a way that it is capable of controlling the display apparatus 12 in such a manner that the display apparatus 12 displays an image that is suitable to simulate the shape of a pupil 24, in particular the pupillary diameter and the position, dependent thereon, of the pupillary midpoint P relative to the chosen reference structure as a function of the intensity of ambient light ascertained by the brightness sensor 26.

As can best be discerned in FIG. 1, the simulator 10 further includes a lens simulation 28, an anterior-eye-chamber simulation 30 and also a cornea simulation 32. The lens simulation 28, the anterior-eye-chamber simulation 30 and the cornea simulation 32 each consist of a synthetic material, into which diffusers have been introduced in order to simulate the scattering behaviour of a natural lens, of a natural anterior eye chamber and of a natural cornea. The lens simulation 28, on the one hand, and the anterior-eye-chamber simulation 30 and also the cornea simulation 32, on the other hand, are arranged on opposite sides of the display apparatus 12. The structural design of the simulator 10 consequently corresponds to the structural design of a natural eye. In particular, the anterior-eye-chamber simulation 30 and the cornea simulation 32 consist of materials that have been chosen in such a way that, for example, differences in refractive index do not result in perturbations of the ophthalmological measurements. Furthermore, the surfaces of these optical elements have been made antireflective and, where appropriate, correspondingly coated.

Figure 2B:
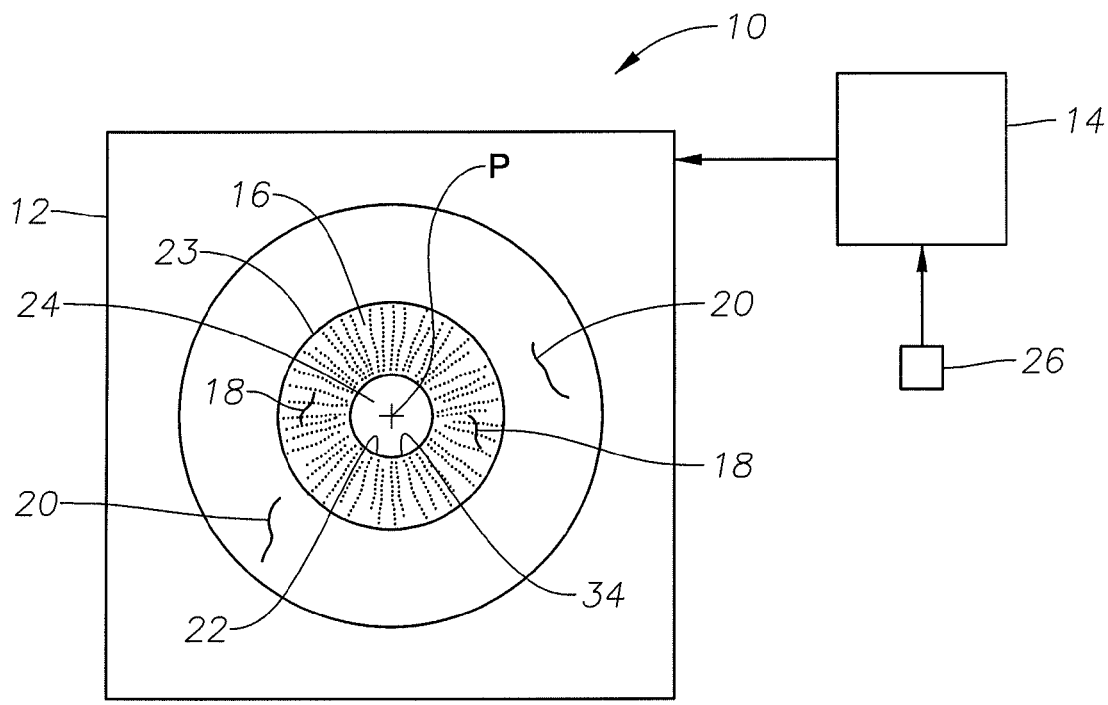

From FIGS. 1 and 2a it can further be gathered that the display apparatus 12 exhibits an aperture 34. By virtue of the aperture 34, at least one portion of the pupil 24 is simulated (see FIG. 2a), in which connection, as represented in FIG. 2b, the pupil 24 can also be simulated completely by the aperture 34 formed in the display apparatus 12. Such a configuration of the simulator 10 has the advantage that in the course of the implementation of an ophthalmological measurement electromagnetic radiation radiated onto the simulator 10 from a source 36 of electromagnetic radiation can be guided onto the lens simulation 28 which is arranged downstream of the display apparatus 12 relative to the direction of propagation of the electromagnetic radiation.

As is further evident from FIG. 1, in the course of the implementation of an ophthalmological measurement with the aid of the simulator 10 the influence exerted on the ray guided from the radiation-source 36 onto the simulator 10 upon passing through the cornea simulation 32, the anterior-eye-chamber simulation 30 and upon impinging on the lens simulation 28 is registered by means of a camera 38. The camera 38 may likewise be used for the purpose of measuring the pupil-centre shift simulated by the simulator 10. Alternatively, however, use may also be made of a separate camera for this purpose.

The invention claimed is:

1. A simulator for simulating a pupil of an eye, comprising:
   a display apparatus;
   a brightness sensor configured to measure the intensity of ambient light;
   a control device configured to:
      receive from the brightness sensor a plurality of measurements of the intensity of ambient light;
      control the display apparatus to display a plurality of images, each image simulating a pupillary midpoint relative to a reference structure of the eye as a function of a measurement of the intensity of ambient light, the plurality of images simulating shifting of the pupillary midpoint as a function of the plurality of measurements by the brightness sensor of the intensity of ambient light; and
   a cornea simulation coupled to the display apparatus, the cornea simulation comprising a synthetic material with a plurality of diffusers that simulate a scattering behavior of a natural cornea.

2. The simulator according to claim 1, wherein each image includes a representation of an iris.

3. The simulator according to claim 1, wherein the reference structure is an apex of a cornea.

4. The simulator according to claim 1, wherein the reference structure is at least one of an outer iris margin, an iris structure, and a blood-vessel structure.

5. The simulator according to claim 1, wherein the display apparatus includes an OLED display.

6. The simulator according to claim 1, wherein the display apparatus includes a foil display.

7. The simulator according to claim 1, wherein the display apparatus exhibits an aperture that simulates at least one portion of the pupil.

8. The simulator of claim 1, further comprising:
   a lens simulation coupled to the display apparatus, the lens simulation comprising a second synthetic material with a plurality of diffusers that simulate a scattering behavior of a natural lens.

9. The simulator of claim 1, further comprising:
   an anterior-eye-chamber simulation coupled to the display apparatus, the anterior-eye-chamber simulation comprising a second synthetic material with a plurality of diffusers that simulate a scattering behavior of a natural anterior eye chamber.

10. A simulator for simulating a pupil of an eye, comprising:
- a lens simulation comprising a first synthetic material with a plurality of diffusers that simulate a scattering behavior of a natural lens;
- an anterior-eye-chamber simulation comprising a second synthetic material with a plurality of diffusers that simulate a scattering behavior of a natural anterior eye chamber;
- a display apparatus disposed between the lens simulation and the anterior-eye-chamber simulation;
- a brightness sensor configured to measure the intensity of ambient light; and
- a control device configured to:
  - receive from the brightness sensor a plurality of measurements of the intensity of ambient light;
  - control the display apparatus to display a plurality of images, each image simulating a pupillary midpoint relative to a reference structure of the eye as a function of a measurement of the intensity of ambient light, the plurality of images simulating shifting of the pupillary midpoint as a function of the plurality of measurements by the brightness sensor of the intensity of ambient light.

11. The simulator of claim 10 further comprising:
- a cornea simulation disposed outwardly from the anterior-eye-chamber simulation, the cornea simulation comprising a third synthetic material with a plurality of diffusers that simulate a scattering behavior of a natural cornea.

12. A simulator for simulating a pupil of an eye, comprising:
- a display apparatus;
- a brightness sensor configured to measure the intensity of ambient light;
- a control device configured to:
  - receive from the brightness sensor a plurality of measurements of the intensity of ambient light;
  - control the display apparatus to display a plurality of images, each image simulating a pupillary midpoint relative to a reference structure of the eye as a function of a measurement of the intensity of ambient light, the plurality of images simulating shifting of the pupillary midpoint as a function of the plurality of measurements by the brightness sensor of the intensity of ambient light; and
- a lens simulation coupled to the display apparatus, the lens simulation comprising a synthetic material with a plurality of diffusers that simulate a scattering behavior of a natural lens.

13. A simulator for simulating a pupil of an eye, comprising:
- a display apparatus;
- a brightness sensor configured to measure the intensity of ambient light;
- a control device configured to:
  - receive from the brightness sensor a plurality of measurements of the intensity of ambient light;
  - control the display apparatus to display a plurality of images, each image simulating a pupillary midpoint relative to a reference structure of the eye as a function of a measurement of the intensity of ambient light, the plurality of images simulating shifting of the pupillary midpoint as a function of the plurality of measurements by the brightness sensor of the intensity of ambient light; and
- an anterior-eye-chamber simulation coupled to the display apparatus, the anterior-eye-chamber simulation comprising a synthetic material with a plurality of diffusers that simulate a scattering behavior of a natural anterior eye chamber.

* * * * *